(12) United States Patent
Yoshino et al.

(10) Patent No.: US 12,275,748 B2
(45) Date of Patent: Apr. 15, 2025

(54) AMIDINATE COMPOUND, DIMER COMPOUND THEREOF, THIN-FILM FORMING RAW MATERIAL, AND METHOD OF PRODUCING THIN FILM

(71) Applicant: ADEKA CORPORATION, Tokyo (JP)

(72) Inventors: Tomoharu Yoshino, Tokyo (JP); Yoshiki Ooe, Tokyo (JP); Keisuke Takeda, Tokyo (JP); Ryota Fukushima, Tokyo (JP); Chiaki Mitsui, Tokyo (JP); Atsushi Yamashita, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 188 days.

(21) Appl. No.: 17/917,671

(22) PCT Filed: Mar. 31, 2021

(86) PCT No.: PCT/JP2021/013898
§ 371 (c)(1),
(2) Date: Oct. 7, 2022

(87) PCT Pub. No.: WO2021/205958
PCT Pub. Date: Oct. 14, 2021

(65) Prior Publication Data
US 2023/0151041 A1    May 18, 2023

(30) Foreign Application Priority Data
Apr. 10, 2020    (JP) ................. 2020-070708

(51) Int. Cl.
| | | |
|---|---|---|
| *C07F 15/06* | (2006.01) | |
| *C01B 33/027* | (2006.01) | |
| *C07F 5/00* | (2006.01) | |
| *C07F 7/02* | (2006.01) | |
| *C07F 7/22* | (2006.01) | |
| *C07F 13/00* | (2006.01) | |
| *C07F 15/04* | (2006.01) | |
| *C23C 16/18* | (2006.01) | |
| *C23C 16/40* | (2006.01) | |
| *C23C 16/455* | (2006.01) | |

(52) U.S. Cl.
CPC .......... *C07F 15/065* (2013.01); *C01B 33/027* (2013.01); *C07F 7/2284* (2013.01); *C23C 16/18* (2013.01); *C23C 16/407* (2013.01); *C23C 16/45553* (2013.01)

(58) Field of Classification Search
CPC ........ C07F 15/065; C07F 5/003; C07F 7/025; C07F 13/005; C07F 15/045; C23C 16/18
See application file for complete search history.

(56) References Cited

U.S. PATENT DOCUMENTS

2010/0092667 A1*   4/2010   Gordon ................. C23C 16/403
                                                                        427/255.6

FOREIGN PATENT DOCUMENTS

| CN | 1726303 | 1/2006 |
| JP | 2006-511716 | 4/2006 |
| JP | 2010-156058 | 7/2010 |
| WO | 2018/088079 | 5/2018 |

OTHER PUBLICATIONS

M. Murthy "New Members of the Periodic Table." 40-41 (2017) ("Murthy") (Year: 2017).*
Helmenstine—2019 (Year: 2019).*
International Search Report issued Jun. 1, 2021 in International (PCT) Application No. PCT/JP2021/013898.
Li et al., "On the Relative Stability of Cobalt- and Nickel-Based Amidinate Complexes against β-Migration", International Journal of Quantum Chemistry, 2009, vol. 109, No. 4, pp. 756-763.

* cited by examiner

*Primary Examiner* — Alexander R Pagano
*Assistant Examiner* — Frank S. Hou
(74) *Attorney, Agent, or Firm* — Wenderoth, Lind & Ponack, L.L.P.

(57) ABSTRACT

The present invention provides an amidinate compound represented by the following general formula (1) or a dimer compound thereof, and a method of producing a thin-film including using the compound as a raw material:

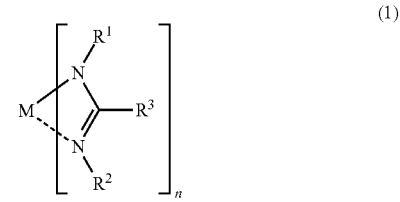

(1)

where $R^1$ and $R^2$ each independently represent an alkyl group having 1 to 5 carbon atoms, $R^3$ represents a hydrogen atom or an alkyl group having 1 to 5 carbon atoms, M represents a metal atom or a silicon atom, and "n" represents the valence of the atom represented by M, provided that at least one hydrogen atom of $R^1$ to $R^3$ is substituted with a fluorine atom.

3 Claims, 2 Drawing Sheets

[Fig. 1]
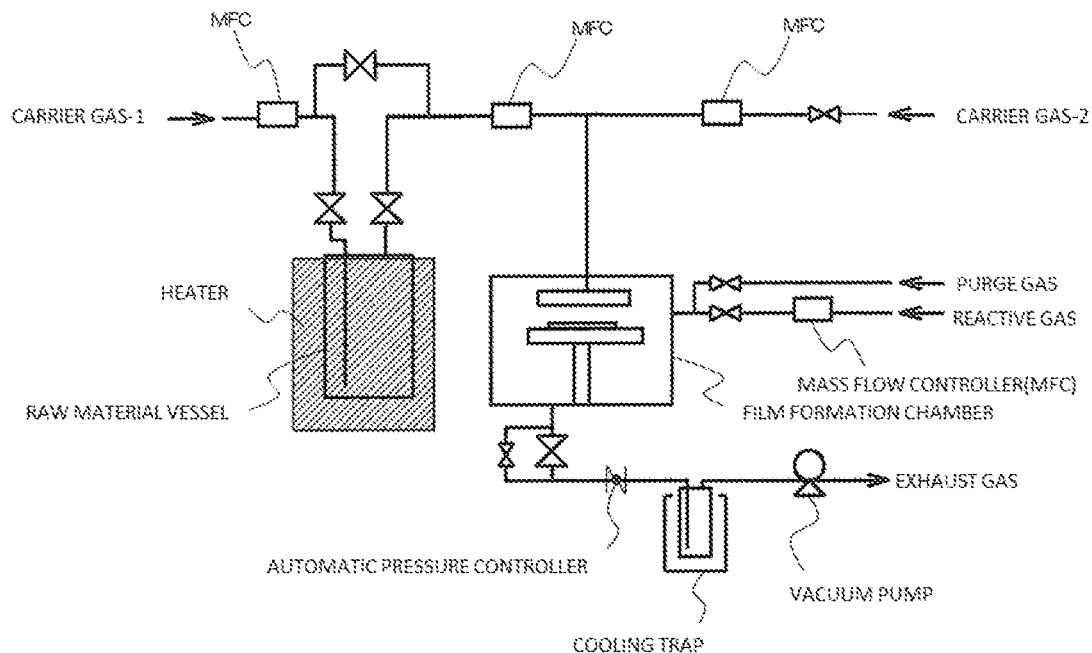
[Fig. 2]
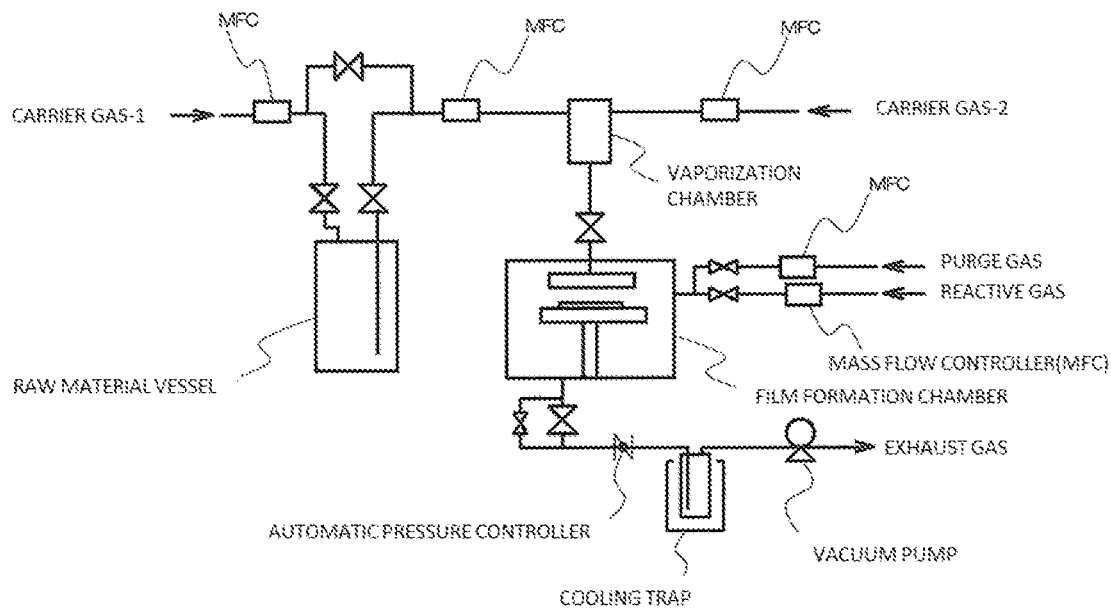

[Fig. 3]
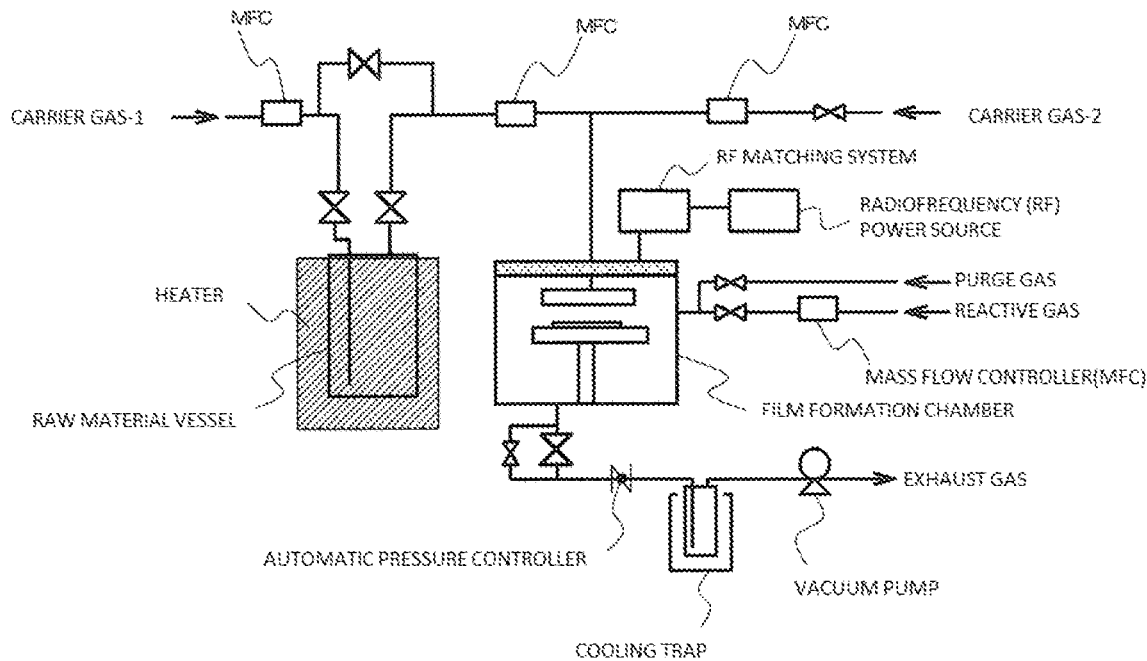
[Fig. 4]
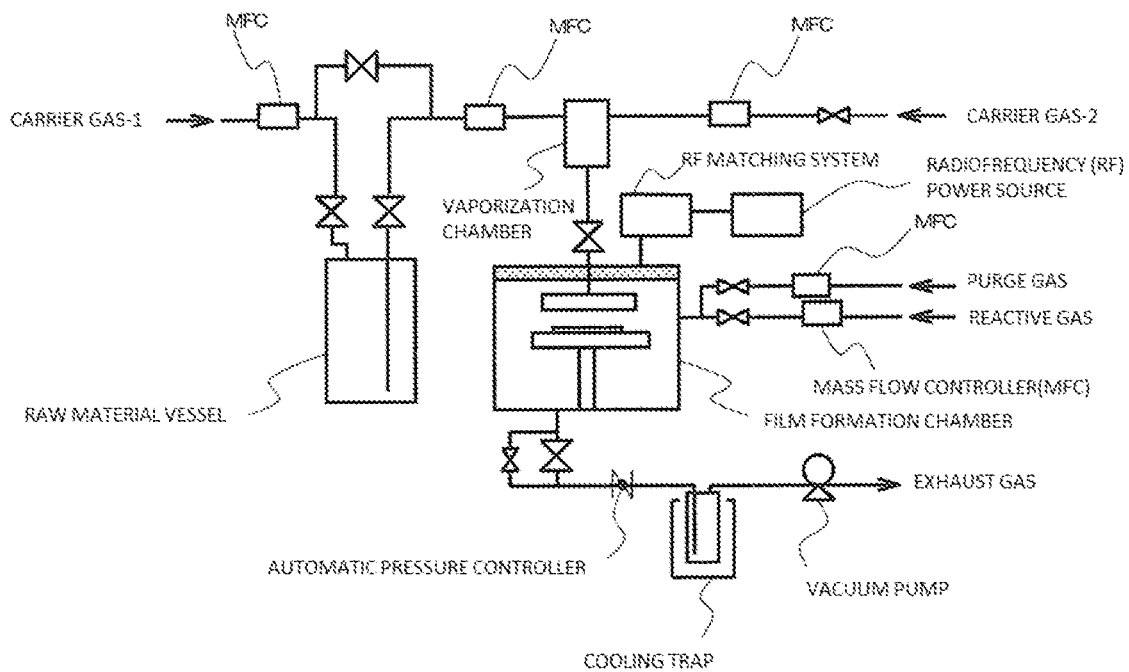

AMIDINATE COMPOUND, DIMER COMPOUND THEREOF, THIN-FILM FORMING RAW MATERIAL, AND METHOD OF PRODUCING THIN FILM

TECHNICAL FIELD

The present invention relates to a novel compound, a thin-film forming raw material containing the compound, and to a method of producing a thin-film including using the thin-film forming raw material.

BACKGROUND ART

A thin-film material containing a metal element or silicon has been used in, for example, a member for an electronic part, such as an electrode film, a resistance film, or a barrier film, a member for a recording medium such as a magnetic film, or an electrode member for a solar cell thin-film or the like because of its excellent electrical characteristics and optical characteristics.

As a method of producing the thin-film, there are given, for example, a sputtering method, an ion plating method, a metal organic decomposition (MOD) method, such as a coating thermal decomposition method or a sol-gel method, and a chemical vapor deposition method. Of those, a chemical vapor deposition (hereinafter sometimes simply referred to as "CVD") method including an atomic layer deposition (ALD) method is an optimum production process because the method has many advantages, such as excellent composition controllability and excellent step coverage, suitability for mass production, and capability of hybrid integration.

Various compounds have been reported as an amidinate compound and a dimer compound thereof to be used in the chemical vapor deposition method. For example, as a raw material for producing a metal cobalt thin-film, in Patent Document 1 and Patent Document 2, there are disclosed, for example, cobalt bis(N,N'-diisopropylacetamidinate), cobalt bis(N,N'-di-sec-butylacetamidinate), a copper (N,N'-diisopropylacetamidinate) dimer, and a copper (N,N'-di-sec-butylacetamidinate) dimer. In addition, in Patent Document 3, there is disclosed a cobalt amidinate compound substituted with an alkyl amino group.

CITATION LIST

Patent Document

[Patent Document 1] JP 2006-511716 A
[Patent Document 2] JP 2010-156058 A
[Patent Document 3] WO 2018/088079 A1

SUMMARY OF INVENTION

Technical Problem

In a method of forming a thin-film through the vaporization of a compound such as the CVD method, important properties that the compound (precursor) to be used as a thin-film forming raw material is required to have are as follows: its vapor pressure is large; its melting point is low (the compound is preferably a liquid at normal temperature); its thermal stability is high; and the compound can produce a high-quality thin-film with high productivity. A thin-film forming raw material containing an amidinate compound or a dimer compound thereof has been required to have a large vapor pressure, a low melting point, and an ability to produce a high-quality thin-film with high productivity when used as a thin-film forming raw material out of those properties. However, the related-art amidinate compound and the dimer compound thereof have not sufficiently satisfied those points.

Accordingly, an object of the present invention is to provide a novel amidinate compound and a dimer compound thereof, which have large vapor pressures, low melting points, and can each produce a high-quality thin-film with high productivity when used as a thin-film forming raw material as compared to the related-art amidinate compound and the dimer compound thereof.

Solution to Problem

The inventors of the present invention have made investigations, and as a result, have found that an amidinate compound and a dimer compound thereof each containing a ligand having a specific structure can solve the above-mentioned problems. Thus, the inventors have reached the present invention.

That is, according to one embodiment of the present invention, there is provided an amidinate compound, which is represented by the following general formula (1), or a dimer compound thereof:

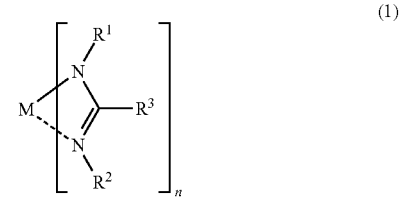

where $R^1$ and $R^2$ each independently represent an alkyl group having 1 to 5 carbon atoms, $R^3$ represents a hydrogen atom or an alkyl group having 1 to 5 carbon atoms, M represents a metal atom or a silicon atom, and "n" represents a valence of the atom represented by M, provided that at least one hydrogen atom of $R^1$ to $R^3$ is substituted with a fluorine atom.

According to one embodiment of the present invention, there is provided a thin-film forming raw material, comprising the above-mentioned compound.

In addition, according to one embodiment of the present invention, there is provided a method of producing a thin-film, the method comprising the steps of: vaporizing the above-mentioned thin-film forming raw material; introducing vapor containing the amidinate compound represented by the general formula (1) or the dimer compound thereof, which has been vaporized, into a treatment atmosphere; and subjecting the compound to decomposition and/or a chemical reaction to form a thin-film containing a metal atom or a silicon atom on a surface of a substrate.

An amidinate compound represented by the following general formula (2) or a dimer compound thereof is identical in meaning to the amidinate compound represented by the general formula (1) or the dimer compound thereof:

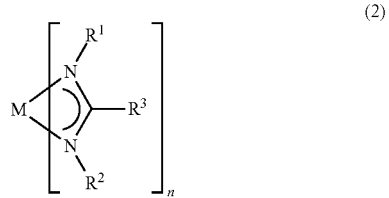

(2)

where $R^1$ and $R^2$ each independently represent an alkyl group having 1 to 5 carbon atoms, $R^3$ represents a hydrogen atom or an alkyl group having 1 to 5 carbon atoms, M represents a metal atom or a silicon atom, and "n" represents a valence of the atom represented by M, provided that at least one hydrogen atom of $R^1$ to $R^3$ is substituted with a fluorine atom.

In addition, an amidinate compound represented by the following general formula (3) is identical in meaning to the amidinate compound represented by the general formula (1) or the dimer compound thereof, the dimer compound being such that "n" represents 1:

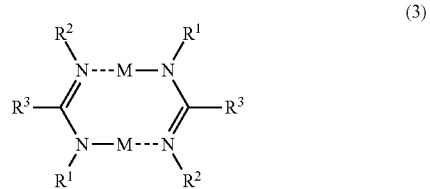

(3)

where $R^1$ and $R^2$ each independently represent an alkyl group having 1 to 5 carbon atoms, $R^3$ represents a hydrogen atom or an alkyl group having 1 to 5 carbon atoms, and M represents a metal atom, provided that at least one hydrogen atom of $R^1$ to $R^3$ is substituted with a fluorine atom.

An amidinate compound represented. by the following general formula (4) is identical in meaning to the amidinate compound represented by the general formula (3):

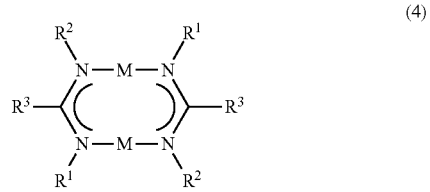

(4)

where $R^1$ and $R^2$ each independently represent an alkyl group having 1 to 5 carbon atoms, $R^3$ represents a hydrogen atom or an alkyl group having 1 to 5 carbon atoms, and M represents a metal atom, provided that at least one hydrogen atom of $R^1$ to $R^3$ is substituted with a fluorine atom.

Advantageous Effects of Invention

According to the present invention, the amidinate compound and the dimer compound thereof, which have high vapor pressures and can each produce a high-quality thin-film with high productivity when used as a thin-film forming raw material as compared to the related-art amidinate compound and the dimer compound thereof, can be provided. The compound of the present invention is suitable as a thin-film forming raw material for a CVD method. In particular, the compound has an ALD window, and is hence excellent as a thin-film forming raw material to be used in an ALD method.

BRIEF DESCRIPTION OF DRAWINGS

FIG. 1 is a schematic diagram for illustrating an example of an ALD apparatus to be used in a method of producing a thin-film according to the present invention.

FIG. 2 is a schematic diagram for illustrating another example of the ALD apparatus to be used in the method of producing a thin-film according to the present invention.

FIG. 3 is a schematic diagram for illustrating still another example of the ALD apparatus to be used in the method of producing a thin-film according to the present invention.

FIG. 4 is a schematic diagram for illustrating yet still another example of the ALD apparatus to be used in the method of producing a thin-film according to the present invention.

DESCRIPTION OF EMBODIMENTS

A compound of the present invention is represented by the general formula (1). The compound of the present invention is suitable as a precursor in a method of producing a thin-film including a vaporization step such as an ALD method, which is one kind of CVD method.

In the general formula (1), $R^1$ and $R^2$ each independently represent an alkyl group having 1 to 5 carbon atoms, $R^3$ represents a hydrogen atom or an alkyl group having 1 to 5 carbon atoms, N represents a metal atom or a silicon atom, and "n" represents a valence of the atom represented by M, provided that at least one hydrogen atom of $R^1$ to $R^3$ substituted with a fluorine atom.

Examples of the "alkyl group having 1 to 5 carbon atoms" include a methyl group, an ethyl group, a propyl group, an isopropyl group, a butyl group, an isobutyl group, a sec-butyl group, a tert-butyl group, a pentyl group, an isopentyl group, and a neopentyl group.

At least one hydrogen atom present in $R^1$ to $R^3$ needs to be substituted with a fluorine atom. Preferably 1 to 9, more preferably 1 to 7, still more preferably 2 to 6, yet still more preferably 3 to 6 hydrogen atoms out of all hydrogen atoms present in $R^1$ to $R^3$ are substituted with fluorine atoms.

For example, an amidinate compound in which 3 hydrogen atoms out of all the hydrogen atoms present in $R^1$ to $R^3$ are substituted with fluorine atoms is included as the amidinate compound of the present invention.

Examples of the alkyl group having 1 to 5 carbon atoms in which at least one hydrogen atom is substituted with a fluorine atom (hereinafter sometimes referred to as "fluoroalkyl group") include a trifluoromethyl group (perfluoromethyl group), a difluoromethyl group, a monofluoromethyl group, a perfluoroethyl group, a 2,2,2-trifluoroethyl group, a 1,1,2,2-tetrafluoroethyl group, a perfluoropropyl group, a 2,2,3,3-tetrafluoropropyl group, a 3,3,3-trifluoropropyl group, a 1,1,1-trifluoroisopropyl group, a 1,1,1,3,3,3 hexafluoroisopropyl group, a 2,2-difluoropropyl group, a 3,3-difluoropropyl group, a 2-fluoropropyl group, a 3-fluoropropyl group, a perfluorobutyl group, a 2,2,3,4,4-pentafluorobutyl group, a 2,2,3,3,4,4,4-heptafluorobutyl group, a 2,2,3,4,4-pentafluorobutyl group, a 3,3,4,4,4-pentafluorobutyl group, a 4,4,4-trifluorobutyl group, a 4,4-difluorobutyl group, a 3,3-difluorobutyl group, a 2,2-difluorobutyl group, a 2-fluorobutyl group, a 3-fluorobutyl group, a 4-fluorobutyl group, a perfluoropentyl group, a 2,2,3,3,4,4, 5,5,5-nonafluoropentyl group, a 2,2,3,3,4,4,5,5-octafluoropentyl group, a 3,3,4,4,5,5,5-heptafluoropentyl group, a 4,4,5,5,5-pentafluoropentyl group, a 5,5,5-trifluoropentyl group, a 5,5-difluoropentyl group, a 2,2-difluoropentyl group, a 3,3-difluoropentyl group, a 4,4-difluoropentyl group, a 2-fluoropentyl group, a 3-fluoropentyl group, a 4-fluoropentyl group, and a 5-fluoropentyl group.

Of those fluoroalkyl groups, a fluoroalkyl group containing a trifluoromethyl ($CF_3$) group is preferred, and specific examples thereof include a trifluoromethyl group, a perfluoroethyl group, a 2,2,2-trifluoroethyl group, a perfluoropropyl group, a 3,3,3-trifluoropropyl group, a 1,1,1-trifluoroisopropyl group, a 1,1,1,3,3,3-hexafluoroisopropyl group, a perfluorobutyl group, a 2,2,3,3,4,4,4-heptafluorobutyl group, a 3,3,4,4,4-pentafluorobutyl group, a 4,4,4-trifluorobutyl group, a perfluoropentyl group, a 3,3,4,4,5,5,5-heptafluoropentyl group, a 4,4,5,5,5-pentafluoropentyl group, and a 5,5,5-trifluoropentyl group.

The amidinate compound of the present invention preferably contains 3 fluorine atoms per compound (except for a dimer thereof). For example, any one of $R^1$ to $R^3$ described above preferably represents a fluoroalkyl group containing a trifluoromethyl ($CF_3$) group. Specifically, any one of $R^1$ to $R^3$ described above preferably represents a trifluoromethyl group, a 2,2,2-trifluoroethyl group, or a 1,1,1-trifluoroisopropyl group.

In the general formula (1), M represents a metal atom or a silicon atom. Examples of the metal atom represented by M include a copper atom, a cobalt atom, a nickel atom, a manganese atom, a zinc atom, a tin atom, a yttrium atom, an indium atom, a titanium atom, and a gallium atom.

In the general formula (1), $R^1$ to $R^3$ and M are each appropriately selected in accordance with a method of producing a thin-film to which the compound is applied. When the compound is used in a method of producing a thin-film including the step of vaporizing the compound, it is preferred to select $R^1$ to $R^3$ and M so that the compound has a large vapor pressure and a low melting point.

$R^1$ represents preferably an alkyl group having 1 to 5 carbon atoms in which at least one hydrogen atom is substituted with a fluorine atom (fluoroalkyl group), more preferably a fluoroalkyl group having 1 to 3 carbon atoms, still more preferably a trifluoromethyl group, a 2,2,2-trifluoroethyl group, or a 1,1,1-trifluoroisopropyl group, most preferably a 2,2,2-trifluoroethyl group because the vapor pressure of the compound is high.

$R^2$ represents preferably an unsubstituted alkyl group having 1 to 5 carbon atoms, more preferably a branched unsubstituted alkyl group having 3 to 5 carbon atoms, most preferably an unsubstituted tert-butyl group because the thermal stability of the compound is high. $R^3$ represents preferably a hydrogen atom or a linear unsubstituted alkyl group having 1 to 5 carbon atoms, more preferably a linear unsubstituted alkyl group having 1 to 3 carbon atoms, particularly preferably a methyl group or an ethyl group, most preferably an ethyl group because the melting point of the compound is low.

M represents preferably a copper atom, a cobalt atom, a nickel atom, a manganese atom, a zinc atom, a tin atom, an yttrium atom, an indium atom, a titanium atom, a gallium atom, or a silicon atom, more preferably a cobalt atom or a tin atom because a high-quality thin-film can be produced with high productivity. In addition, because a high-quality thin-film can be produced with high productivity, when M represents a copper atom, the compound represented by the general formula (1) is preferably a dimer compound, and when M represents a cobalt atom, a nickel atom, a manganese atom, a zinc atom, a tin atom, an yttrium atom, an indium atom, a titanium atom, a gallium atom, or a silicon atom, the compound represented by the general formula (1) is preferably a monomer compound. In other words, when "n" in the general formula (1) represents 1, the compound represented by the general formula (1) is preferably a dimer compound, and when "n" represents 2 or more, the compound represented by the general formula (1) is preferably a monomer compound.

"n" in the general formula (1) represents the valence of the atom represented by M. For example, "n" represents preferably from 1 to 6, more preferably from 1 to 4, still more preferably from 1 to 3, most preferably 2.

In addition, when the compound is used in a method of producing a thin-film by a MOD method free of any vaporization step, $R^1$ to $R^3$ may each be arbitrarily selected in accordance with, for example, solubility in a solvent to be used and a thin-film formation reaction.

Preferred specific examples of the compound represented by the general formula (1) include Compounds No. 1 to No. 132 below. In Compounds No. 1 to No. 132 below, "Me" represents a methyl group, "Et" represents an ethyl group, "nPr" represents a n-propyl group, and "iPr" represents an isopropyl group.

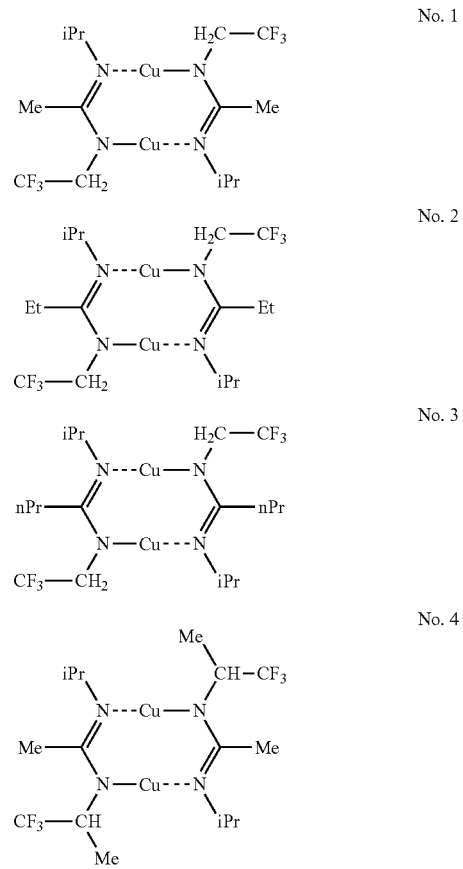

No. 5
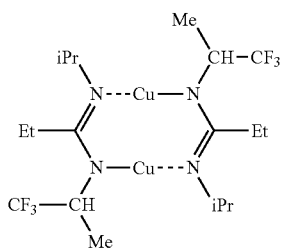
No. 6
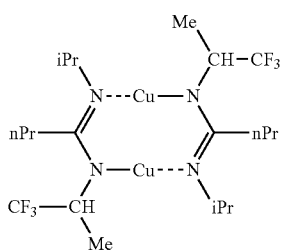
No. 7
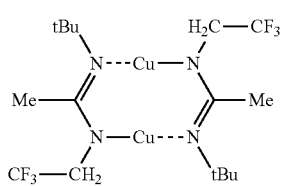
No. 8
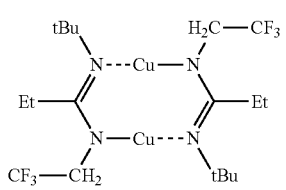
No. 9
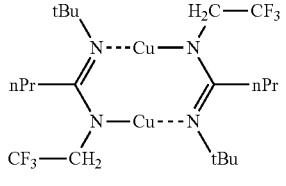
No. 10
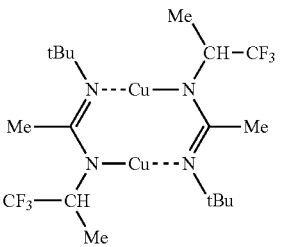
No. 11
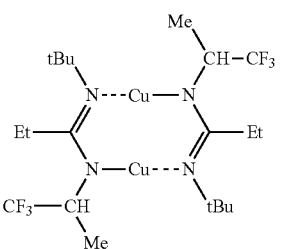
No. 12
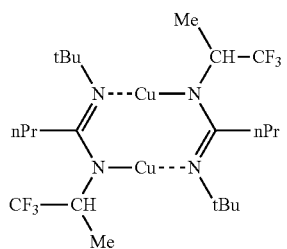
No. 13
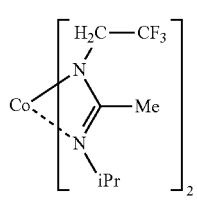
No. 14
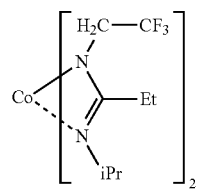
No. 15
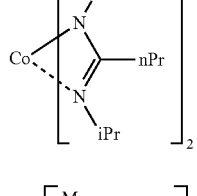
No. 16
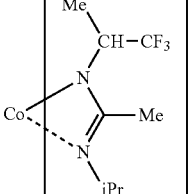
No. 17
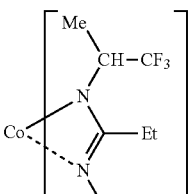
No. 18
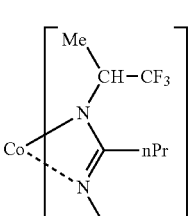

-continued
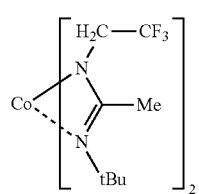 No. 19
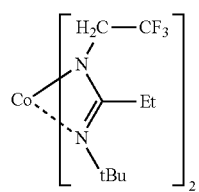 No. 20
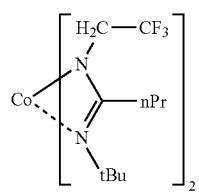 No. 21
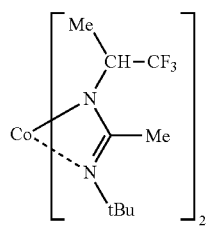 No. 22
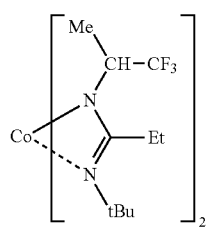 No. 23
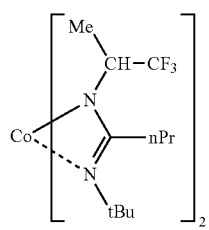 No. 24
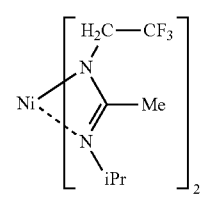 No. 25
-continued
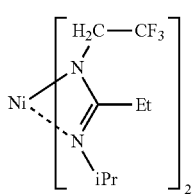 No. 26
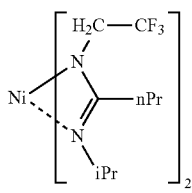 No. 27
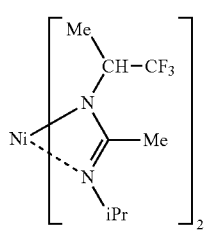 No. 28
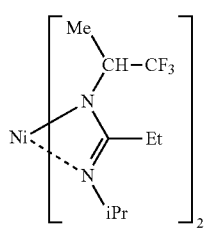 No. 29
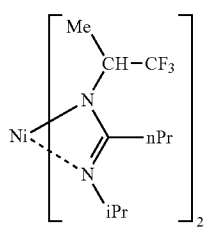 No. 30
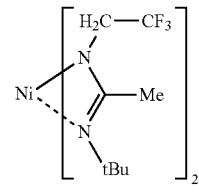 No. 31
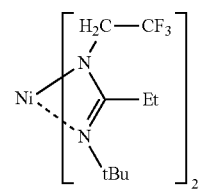 No. 32

No. 33
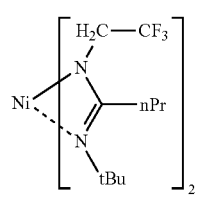
No. 34
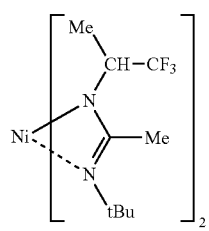
No. 35
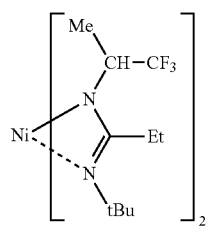
No. 36
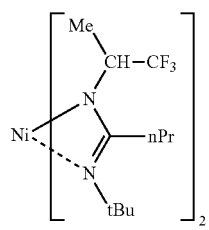
No. 37
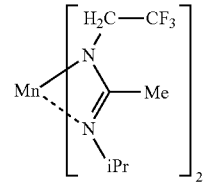
No. 38
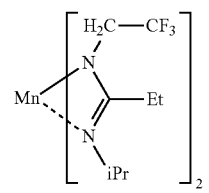
No. 39
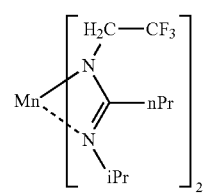
No. 40
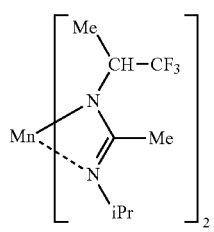
No. 41
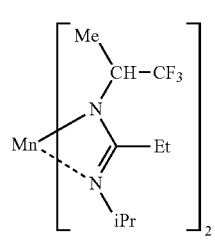
No. 42
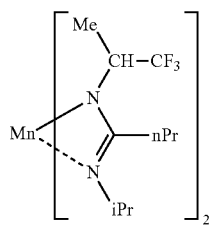
No. 43
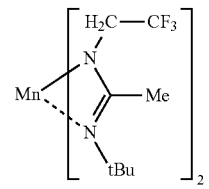
No. 44
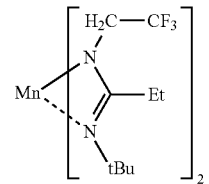
No. 45
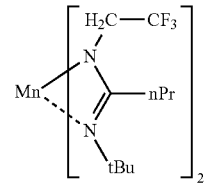
No. 46
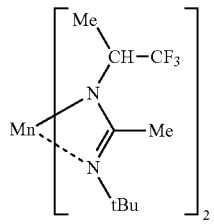

-continued
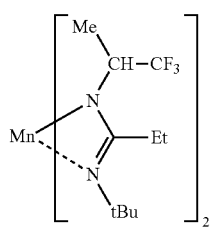
No. 47
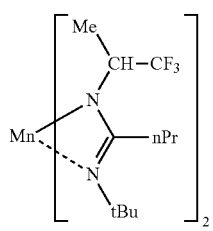
No. 48
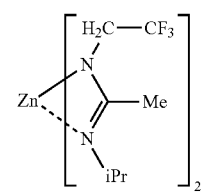
No. 49
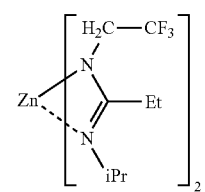
No. 50
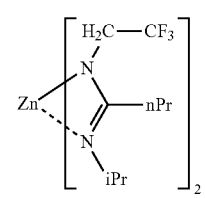
No. 51
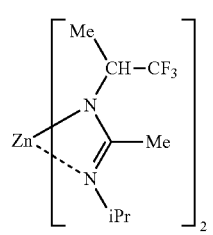
No. 52
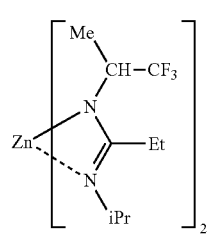
No. 53
-continued
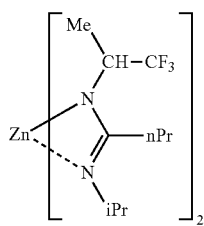
No. 54
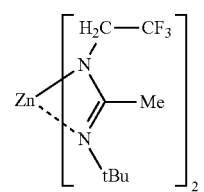
No. 55
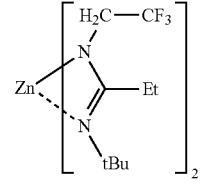
No. 56
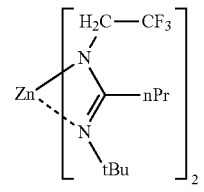
No. 57
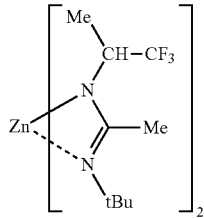
No. 58
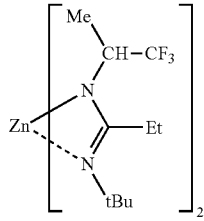
No. 59
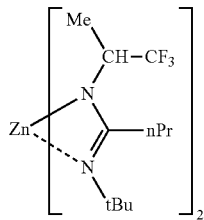
No. 60

-continued
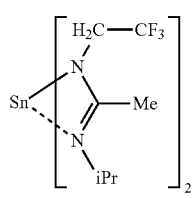 No. 61
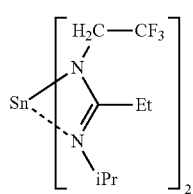 No. 62
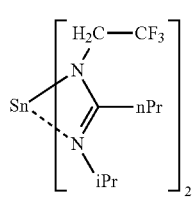 No. 63
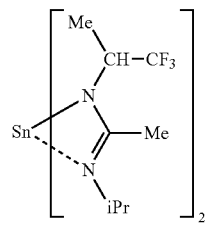 No. 64
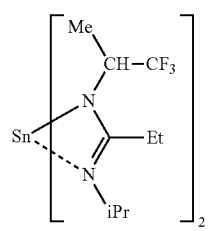 No. 65
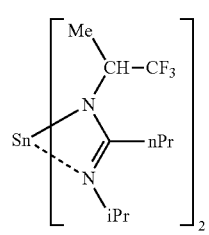 No. 66
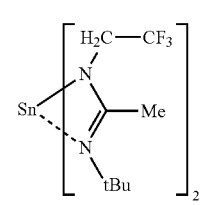 No. 67
-continued
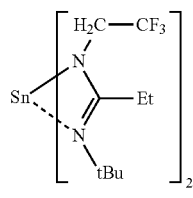 No. 68
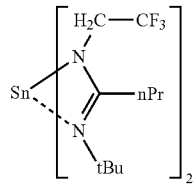 No. 69
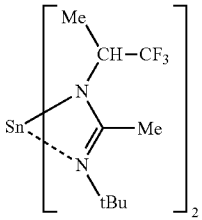 No. 70
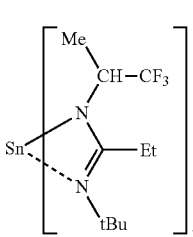 No. 71
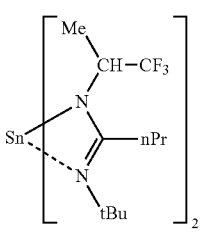 No. 72
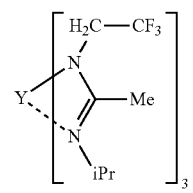 No. 73
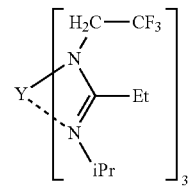 No. 74

-continued
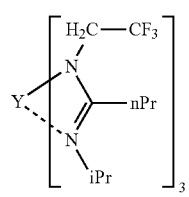 No. 75
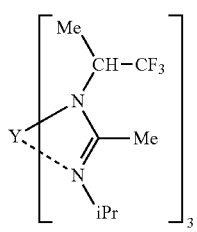 No. 76
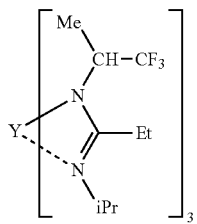 No. 77
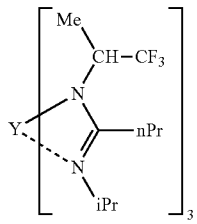 No. 78
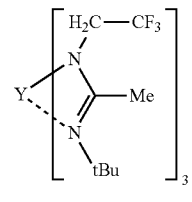 No. 79
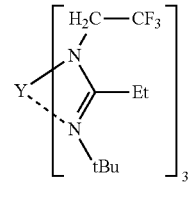 No. 80
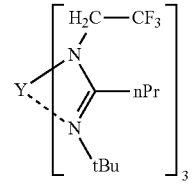 No. 81
-continued
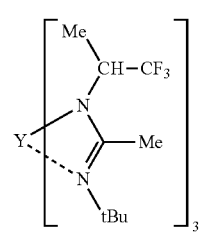 No. 82
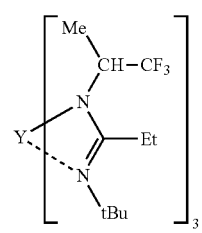 No. 83
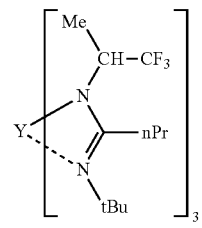 No. 84
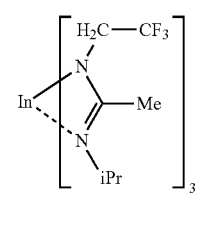 No. 85
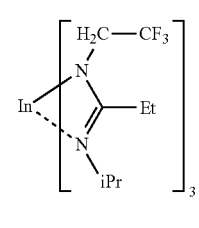 No. 86
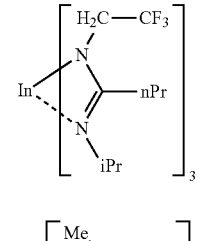 No. 87
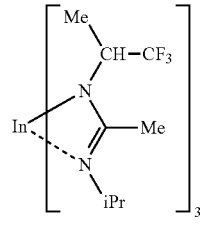 No. 88

-continued
No. 89
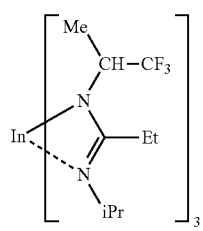
No. 90
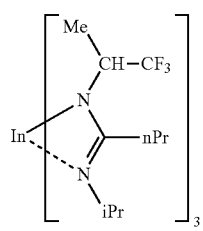
No. 91
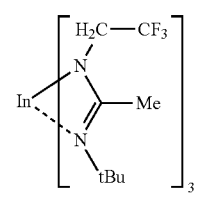
No. 92
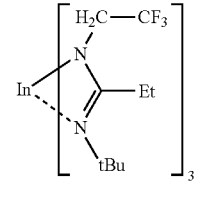
No. 93
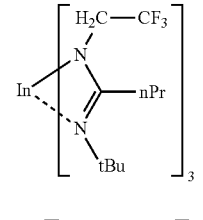
No. 94
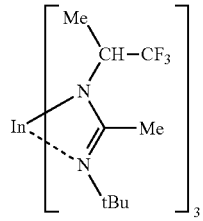
No. 95
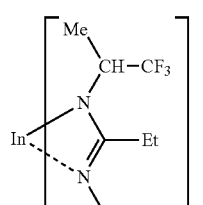
-continued
No. 96
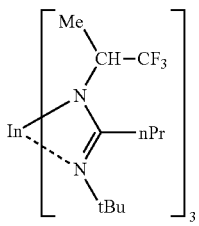
No. 97
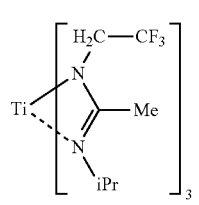
No. 98
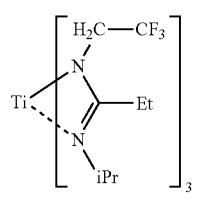
No. 99
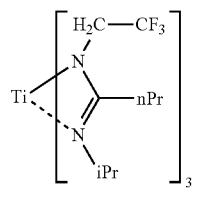
No. 100
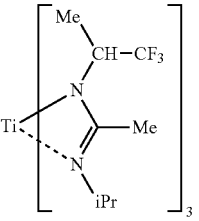
No. 101
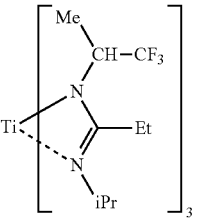
No. 102
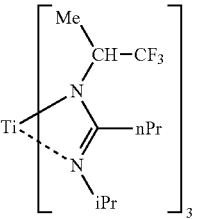

| | |
|---|---|
| 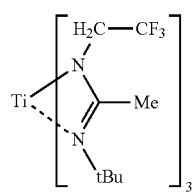 No. 103 | 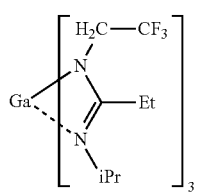 No. 110 |
| 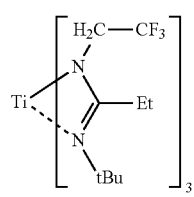 No. 104 | 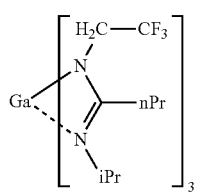 No. 111 |
| 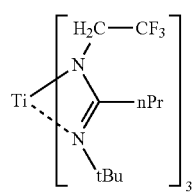 No. 105 | 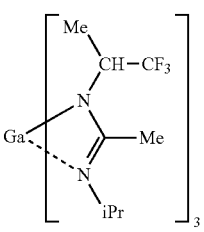 No. 112 |
| 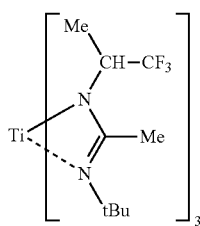 No. 106 | 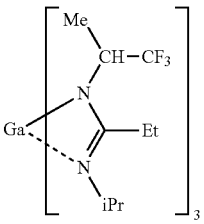 No. 113 |
| 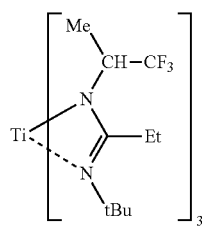 No. 107 | 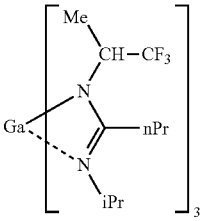 No. 114 |
| 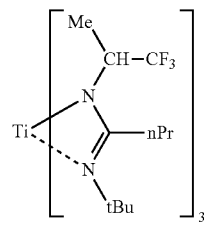 No. 108 | 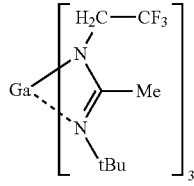 No. 115 |
| 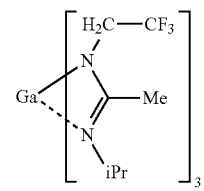 No. 109 | 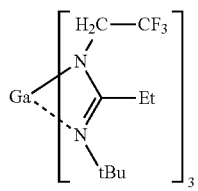 No. 116 |

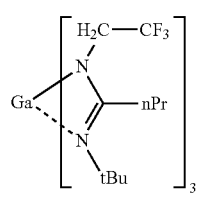 No. 117
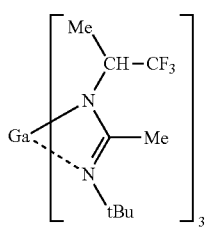 No. 118
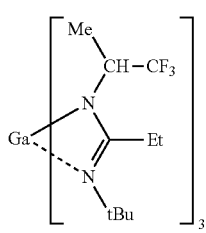 No. 119
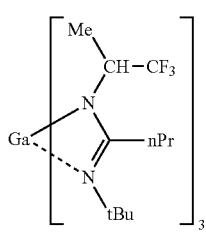 No. 120
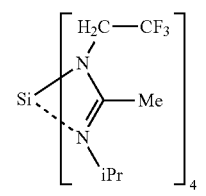 No. 121
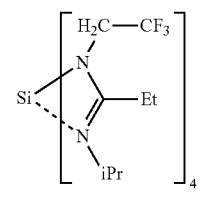 No. 122
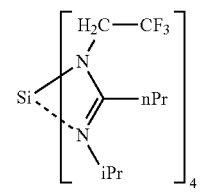 No. 123
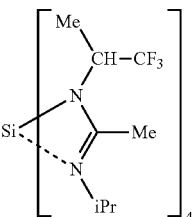 No. 124
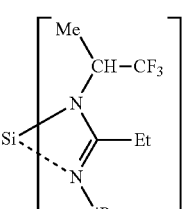 No. 125
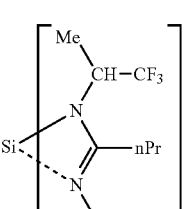 No. 126
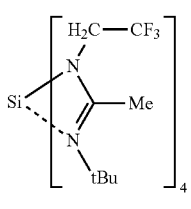 No. 127
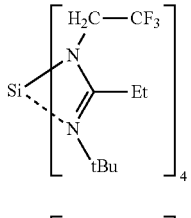 No. 128
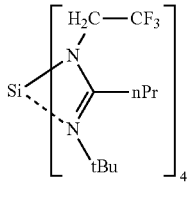 No. 129
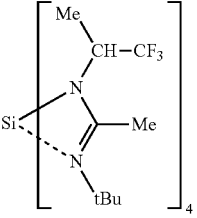 No. 130

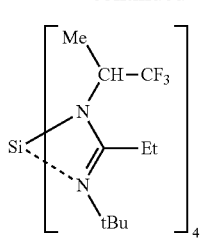

No. 131

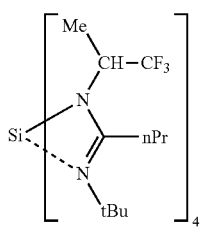

No. 132

A method of producing the compound represented by the general formula (1) is not particularly limited, and the compound is produced by applying a well-known reaction. For example, the compound may be obtained as described below. Under a dichloromethane solvent, iron chloride, a nitrile compound having a corresponding structure, an alkyl halide compound having a corresponding structure, and a fluorine-containing amine compound having a corresponding structure are caused to react with each other, and the resultant is purified to provide an intermediate compound. After that, under a tetrahydrofuran solvent, the resultant intermediate compound, the chloride of the corresponding metal, and an alkyllithium are caused to react with each other. After that, the resultant is filtered, and the solvent is evaporated from the filtrate, followed by the purification of the residue by distillation to provide the compound.

The nitrile compound is represented by $R^4$—CN, and $R^4$ has a group corresponding to $R^3$ in the general formula (1). The alkyl halide compound is represented by $R^5$—X, $R^5$ has a group corresponding to $R^2$ in the general formula (1), and X represents a halogen. The fluorine-containing amine compound is represented by $R^6$—$NH_2$, and $R^6$ has a group corresponding to $R^1$ in the general formula (1).

Next, a thin-film forming raw material of the present invention is described. The thin-film forming raw material of the present invention contains the compound represented by the general formula (1) as a precursor of a thin-film. The form of the thin-film forming raw material varies depending on a production process to which the thin-film forming raw material is applied. For example, when a thin-film containing only a metal atom or a silicon atom as a metal is produced, the thin-film forming raw material of the present invention is free of a metal compound other than the compound represented by the general formula (1) and a semimetal compound. Meanwhile, when a thin-film containing two or more kinds of metals and/or a semimetal is produced, the thin-film forming raw material of the present invention may contain a compound containing a desired metal and/or a compound containing the semimetal (hereinafter sometimes referred to as "other precursor") in addition to the compound represented by the general formula (1). The thin-film forming raw material of the present invention may further contain an organic solvent and/or a nucleophilic reagent as described later. As described above, the physical properties of the compound represented by the general formula (1) serving as the precursor are suitable for a CVD method, and hence the thin-film forming raw material of the present invention is useful as a chemical vapor deposition raw material (hereinafter sometimes referred to as "CVD raw material"). In particular, the thin-film forming raw material of the present invention is particularly suitable for an ALD method because the compound represented by the general formula (1) has an ALD window.

When the thin-film forming raw material of the present invention is a chemical vapor deposition raw material, the form thereof is appropriately selected depending on a procedure such as a transportation and supply method of the CVD method to be used.

As the above-mentioned transportation and supply method, there are given a gas transportation method and a liquid transportation method. The gas transportation method involves heating and/or decompressing the CVD raw material in a vessel in which the raw material is stored (hereinafter sometimes referred to as "raw material vessel"), to thereby vaporize the raw material to obtain a raw material gas, and introducing the raw material gas into a film formation chamber (hereinafter sometimes referred to as "deposition reaction portion") having a substrate set therein together with a carrier gas, such as argon, nitrogen, or helium, to be used as required. The liquid transportation method involves transporting the CVD raw material to a vaporization chamber under the state of a liquid or a solution, heating and/or decompressing the raw material in the vaporization chamber, to thereby vaporize the raw material to obtain a raw material gas, and introducing the raw material gas into the film formation chamber. In the case of the gas transportation method, the compound represented by the general formula (1) itself may be used as the CVD raw material. In the case of the liquid transportation method, the compound represented by the general formula (1) itself or a solution obtained by dissolving the compound in an organic solvent may be used as the CVD raw material. Any such CVD raw material may further contain the other precursor, a. nucleophilic reagent, and the like.

In addition, in a multi-component CVD method, there are given a method involving vaporizing and supplying the CVD raw material independently for each component (hereinafter sometimes referred to as "single source method"), and a method involving vaporizing and supplying a mixed raw material obtained by mixing a multi-component raw material with desired composition in advance (hereinafter sometimes referred to as "cocktail source method"). In the case of the cocktail source method, a mixture of the compound represented by the general formula (1) and the other precursor or a mixed solution obtained by dissolving the mixture in an organic solvent may be used as the CVD raw material. The mixture or the mixed solution may further contain a nucleophilic reagent and the like.

There is no particular limitation on the above-mentioned organic solvent, and a well-known general organic solvent may be used. Examples of the organic solvent include: acetic acid esters, such as ethyl acetate, butyl acetate, and methoxyethyl acetate; ethers, such as tetrahydrofuran, tetrahydropyran, ethylene glycol dimethyl ether, diethylene glycol dimethyl ether, triethylene glycol dimethyl ether, dibutyl ether, and dioxane; ketones, such as methyl butyl ketone, methyl isobutyl ketone, ethyl butyl ketone, dipropyl ketone, diisobutyl ketone, methyl amyl ketone, cyclohexanone, and methylcyclohexanone; hydrocarbons, such as hexane, cyclohexane, methylcyclohexane, dimethylcyclohexane, ethylcyclohexane, heptane, octane, toluene, and xylene; hydrocarbons each having a cyano group, such as 1-cyanopropane, 1-cyanobutane, 1-cyanohexane, cyanocyclohexane, cyanobenzene, 1,3-dicyanopropane, 1,4-dicyanobutane, 1,6-dicyanohexane, 1,4-dicyanocyclohexane, and 1,4-dicyanobenzene; and pyridine and lutidine. Those organic solvents may be used alone or as a mixture thereof depending on the solubility of a solute, a relationship among the use temperature, boiling point, and flash point of each of the solvents, and the like.

When the thin-film forming raw material of the present invention is a mixed solution with the above-mentioned organic solvent, the amount of the entire precursors in the thin-film forming raw material is preferably from 0.01 mol/liter to 2.0 mol/liter, more preferably from 0.05 mol/liter to 1.0 mol/liter.

When the thin-film forming raw material of the present invention is free of a metal compound other than the compound represented by the general formula (1) and a semimetal compound, the amount of the entire precursors herein means the amount of the compound represented by the general formula (1).

When the thin-film forming raw material of the present invention contains a compound containing another metal and/or a compound containing a semimetal (other precursor) in addition to the compound represented by the general formula (1), the amount of the entire precursors herein means the total amount of the compound represented by the general formula (1) and the other precursor.

In addition, in the case of the multi-component CVD method, there is no particular limitation on the other precursor to be used together with the compound represented by the general formula (1), and a well-known general precursor used in the CVD raw material may be used.

Examples of the other precursor include compounds obtained from one or more kinds selected from the group consisting of compounds used as organic ligands, such as an alcohol compound, a glycol compound, a β-diketone compound, a cyclopentadiene compound, and an organic amine compound, and silicon or a metal. Examples of the kind of the metal in the precursor include lithium, sodium, potassium, magnesium, calcium, strontium, barium, titanium, zirconium, hafnium, vanadium, tantalum, chromium, molybdenum, tungsten, manganese, iron, cobalt, rhodium, iridium, nickel, palladium, platinum, copper, silver, gold, zinc, aluminum, germanium, tin, lead, antimony, bismuth, yttrium, lanthanum, cerium, praseodymium, neodymium, promethium, samarium, europium, gadolinium, terbium, dysprosium, holmium, erbium, thulium, ytterbium, ruthenium, and lutetium.

Examples of the alcohol compound to be used as the organic ligand in the above-mentioned other precursor include: alkyl alcohols, such as methanol, ethanol, propanol, isopropyl alcohol, butanol, sec-butyl alcohol, isobutyl alcohol, tert-butyl alcohol, pentyl alcohol, isopentyl alcohol, and tert-pentyl alcohol; ether alcohols, such as 2-methoxyethanol, 2-ethoxyethanol, 2-butoxyethanol, 2-(2-methoxyethoxy)ethanol, 2-methoxy-1-methylethanol, 2-methoxy-1,1-dimethylethanol, 2-ethoxy-1,1-dimethylethanol, 2-isopropoxy-1,1-dimethylethanol, 2-butoxy-1,1-dimethylethanol, 2-(2-methoxyethoxy)-1,1-dimethylethanol, 2-propoxy-1,1-diethylethanol, 2-s-butoxy-1,1-diethylethanol, and 3-methoxy-1,1-dimethvipropanol; and dialkylamino alcohols, such as dimethylaminoethanol, ethylmethylaminoethanol, diethylaminoethanol, dimethylamino-2-pentanol, ethylmethylamino-2-pentanol, dimethylamino-2-methyl-2-pentanol, ethylmethylamino-2-methyl-2-pentanol, and diethylamino-2-methyl-2-pentanol.

Examples of the glycol compound to be used as the organic ligand in the above-mentioned other precursor include 1,2-ethanediol, 1,2-propanediol, 1,3-propanediol, 2,4-hexanediol, 2,2-dimethyl-1,3-propanediol, 2,2-diethyl-1,3-propanediol, 1,3-butanediol, 2,4-butanediol, 2,2-diethyl-1,3-butanediol, 2-ethyl-2-butyl-1,3-propanediol, 2,4-pentanediol, 2-methyl-1,3-propanediol, 2-methyl-2,4-pentanediol, 2,4-hexanediol, and 2,4-dimethyl-2,4-pentanediol.

Examples of the β-diketone compound to be used as the organic ligand in the above-mentioned other precursor include: alkyl-substituted β-diketones, such as acetylacetone, hexane-2,4-dione, 5-methylhexane-2,4-dione, heptane-2,4-dione, 2-methylheptane-3,5-dione, 5-methylheptane-2,4-dione, 6-methylheptane-2,4-dione, 2,2-dimethylheptane-3,5-dione, 2,6-dimethylheptane-3,5-dione, 2,2,6-trimethylheptane-3,5-dione, 2,2,6,6-tetramethylheptane-3,5-dione, octane-2,4-dione, 2,2,6-trimethyloctane-3,5-dione, 2,6-dimethyloctane-3,5-dione, 2,9-dimethylnonane-4,6-dione, 2-methyl-6-ethyldecane-3,5-dione, and 2,2-dimethyl-6-ethyldecane-3,5-dione; fluorine-substituted alkyl β-diketones, such as 1,1,1-trifluoropentane-2,4-dione, 1,1,1-trifluoro-5,5-dimethylhexane-2,4-dione, 1,1,1,5,5,5-hexafluoropentane-2,4-dione, and 1,3-diperfluorohexylpropane-1,3-dione; and ether-substituted β-diketones, such as 1,1,5,5-tetramethyl-1-methoxyhexane-2,4-dione, 2,2,6,6-tetramethyl-1-methoxyheptane-3,5-dione, and 2,2,6,6-tetramethyl-1-(2-methoxyethoxy)heptane-3,5-dione.

Examples of the cyclopentadiene compound to be used as the organic ligand in the above-mentioned other precursor include cyclopentadiene, methylcyclopentadiene, ethylcyclopentadiene, propylcyclopentadiene, isopropylcyclopentadiene, butylcyclopentadiene, sec-butylcyclopentadiene, isobutylcyclopentadiene, tert-butylcyclopentadiene, dimethylcyclopentadiene, and tetramethylcyclopentadiene.

Examples of the organic amine compound to be used as the organic ligand in the above-mentioned other precursor include methylamine, ethylamine, propvlamine, isopropylamine, butylamine, sec-butylamine, tert-butylamine, isobutylamine, dimethylamine, diethylamine, dipropylamine, diisopropylamine, ethylmethylamine, propylmethylamine, and isopropylmethylamine.

The above-mentioned other precursors are known in the art, and production methods therefor are also known. An example of the production methods is given below. For example, when the alcohol compound is used as the organic ligand, the precursor may be produced through a reaction between an inorganic salt of the metal described above or a hydrate thereof and an alkali metal alkoxide of the alcohol compound. In this case, examples of the inorganic salt of the metal or the hydrate thereof may include a halide and a nitrate of the metal, and examples of the alkali metal alkoxide may include a sodium alkoxide, a lithium alkoxide, and a potassium alkoxide.

In the case of the single source method, a compound similar to the compound represented by the general formula (1) in the behavior of thermal decomposition and/or oxidative decomposition is preferably used as the above-mentioned other precursor. In the case of the cocktail source method, a compound that not only is similar to the compound represented by the general formula (1) in the behavior of thermal decomposition and/or oxidative decomposition but also does not cause any change impairing desired characteristics as a precursor through a chemical reaction or the like at the time of mixing is preferably used as the above-mentioned other precursor.

In addition, the thin-film forming raw material of the present invention may contain a nucleophilic reagent as required in order to impart stability to the compound represented by the general formula (1) and the other precursor. Examples of the nucleophilic reagent include: ethylene glycol ethers, such as glyme, diglyme, triglyme, and tetraglyme; crown ethers, such as 18-crown-6, dicyclohexyl-18-crown-6, 24-crown-8, dicyclohexyl-24-crown-8, and dibenzo-24-crown-8; polyamines, such as ethylenediamine, N,N'-tetramethylethylenediamine, diethylenetriamine, triethylenetetramine, tetraethylenepentamine, pentaethylenehexamine, 1,1,4,7,7-pentamethyldiethylenetriamine, 1,1,4,7,10,10-hexamethyltriethylenetetramine, and triethoxytriethyleneamine; cyclic polyamines, such as cyclam and cyclen; heterocyclic compounds, such as pyridine, pyrrolidine, piperidine, morpholine, N-methylpyrrolidine, N-methylpiperidine, N-methylmorpholine, tetrahydrofuran, tetrahydropyran, 1,4-dioxane, oxazole, thiazole, and oxathiolane; β-keto esters, such as methyl acetoacetate, ethyl acetoacetate, and 2-methoxyethyl acetoacetate; and β-diketones, such as acetylacetone, 2,4-hexanedione, 2,4-heptanedione, 3,5-heptanedione, and dipivaloylmethane. The usage amount of each of those nucleophilic reagents is preferably from 0.1 mol to 10 mol, more preferably from 1 mol to 4 mol with respect to 1 mol of the amount of the entire precursors.

The thin-film forming raw material of the present invention is prevented from containing impurity metal elements other than the components forming the raw material, impurity halogens, such as impurity chlorine, and impurity organic substances to the extent possible. The content of each of the impurity metal elements is preferably 100 ppb or less, more preferably 10 ppb or less, and the total content thereof is preferably 1 ppm or less, more preferably 100 ppb or less. In particular, when the raw material is used as a gate insulating film, a gate film, or a barrier layer of an LSI, it is required to reduce the contents of alkali metal elements and alkaline-earth metal elements that influence the electrical characteristics of a thin-film to be obtained. The content of the impurity halogens is preferably 100 ppm or less, more preferably 10 ppm or less, most preferably 1 ppm or less. The total content of the impurity organic substances is preferably 500 ppm or less, more preferably 50 ppm or less, most preferably 10 ppm or less. In addition, moisture causes generation of particles in the chemical vapor deposition raw material and generation of particles during thin-film formation. Accordingly, moisture in each of the precursor, the organic solvent, and the nucleophilic reagent is preferably removed as much as possible before its use. The moisture content of each of the precursor, the organic solvent, and the nucleophilic reagent is preferably 10 ppm or less, more preferably 1 ppm or less.

In addition, it is preferred that the thin-film forming raw material of the present invention be prevented from containing particles to the extent possible in order to reduce or prevent particle contamination of a thin-film to be formed. Specifically, in particle measurement with a light scattering liquid particle detector in a liquid phase, it is preferred that the number of particles larger than 0.3 μm be 100 or less in 1 mL of the liquid phase, it is more preferred that the number of particles larger than 0.2 μm be 1,000 or less in 1 mL of the liquid phase, and it is most preferred that the number of particles larger than 0.2 μm be 100 or less in 1 mL of the liquid phase.

Next, a method of producing a thin-film including using the thin-film forming raw material of the present invention is described. A method of producing a thin-film of the present invention is a CVD method including: introducing a raw material gas obtained by vaporizing the thin-film forming raw material of the present invention and a reactive gas to be used as required into a film formation chamber (treatment atmosphere) having a substrate set therein; and then subjecting the precursor in the raw material gas to decomposition and/or a chemical reaction on the substrate, to thereby grow and deposit a thin-film containing a metal atom or a silicon atom on the surface of the substrate. There are no particular limitations on a transportation and supply method for the raw material, a deposition method therefor, production conditions, a production apparatus, and the like, and well-known general conditions and methods may be used.

Examples of the above-mentioned reactive gas to be used as required include: oxidizing gases, such as oxygen, ozone, and water vapor; reducing gases, such as a hydrocarbon compound, for example, methane or ethane, hydrogen, carbon monoxide, and an organic metal compound; and nitriding gases, such as an organic amine compound, for example, a monoalkylamine, a dialkylamine, a trialkylamine, or an alkylenediamine, hydrazine, and ammonia. Those reactive gases may be used alone or as a mixture thereof. The compound represented by the general formula (1) has such a property as to satisfactorily react with the oxidizing gas or the reducing gas, and has such a property as to particularly satisfactorily react with water vapor or hydrogen. Accordingly, the oxidizing gas or the reducing gas is preferably used as the reactive gas, and water vapor or hydrogen is particularly preferably used.

In addition, examples of the above-mentioned transportation and supply method include the gas transportation method, the liquid transportation method, the single source method, and the cocktail source method described above.

In addition, examples of the above-mentioned deposition method include: thermal CVD including causing a raw material gas, or the raw material gas and a reactive gas, to react only with heat, to thereby deposit a thin-film; plasma CVD using heat and plasma; optical CVD using heat and light; optical plasma CVD using heat, light, and plasma; and ALD including dividing a deposition reaction of CVD into elementary steps, and performing deposition at a molecular level in a stepwise manner.

As a material for the substrate, there are given, for example: silicon; ceramics, such as silicon nitride, titanium nitride, tantalum nitride, titanium oxide, titanium nitride, ruthenium oxide, zirconium oxide, hafnium oxide, and lanthanum oxide; glass; and metals such as metal cobalt. The shape of the substrate is, for example, a plate shape, a spherical shape, a fibrous shape, or a scaly shape. The surface of the substrate may be planar, or may have a three-dimensional structure such as a trench structure.

In addition, examples of the above-mentioned production conditions include a reaction temperature (substrate temperature), a reaction pressure, and a deposition rate. The reaction temperature is preferably from room temperature to 500° C., more preferably from 100° C. to 300° C. In addition, the reaction pressure is preferably from 10 Pa to an atmospheric pressure in the case of the thermal CVD or the optical CVD, and is preferably from 10 Pa to 2,000 Pa in the case of using plasma.

In addition, the deposition rate may be controlled by the supply conditions (vaporization temperature and vaporization pressure) of the raw material, the reaction temperature, and the reaction pressure. When the deposition rate is large, the characteristics of a thin-film to be obtained may deteriorate. When the deposition rate is small, a problem may occur in productivity. Accordingly, the deposition rate is preferably from 0.01 nm/min to 100 nm/min, more preferably from 1 nm/min to 50 nm/min. In addition, in the case of the ALD method, the deposition rate is controlled by the number of cycles so that a desired film thickness may be obtained.

Further, as the above-mentioned production conditions, there are given a temperature and a pressure when the thin-film forming raw material is vaporized to obtain a raw material gas. The step of vaporizing the thin-film forming raw material to obtain a raw material gas may be performed in the raw material vessel or in the vaporization chamber. In any case, it is preferred that the thin-film forming raw material of the present invention be evaporated at a temperature of from 0° C. to 150° C. In addition, when the thin-film forming raw material is vaporized to obtain a raw material gas in the raw material vessel or in the vaporization chamber, the pressure in the raw material vessel and the pressure in the vaporization chamber are each preferably from 1 Pa to 10,000 Pa.

When the ALD method is adopted, the method of producing a thin-film of the present invention may include, in addition to a raw material introduction step of vaporizing the thin-film forming raw material by the above-mentioned transportation and supply method to provide a raw material gas, followed by the introduction of the raw material gas into the film formation chamber, a precursor thin-film formation step of forming a precursor thin-film from the above-mentioned compound in the raw material gas on the surface of the above-mentioned substrate, an evacuation step of evacuating an unreacted compound gas, and a metal-containing thin-film formation step of causing the precursor thin-film to chemically react with the reactive gas, to thereby form a thin-film containing a metal on the surface of the substrate.

Now, regarding each step of the ALD method, the case of forming a metal thin-film is described in detail as an example. First, the above-mentioned raw material introduction step is performed. A preferred temperature and pressure when the thin-film forming raw material is turned into a raw material gas are the same as those described in the method of producing a thin-film by the CVD method. Next, the raw material gas introduced into the film formation chamber and the surface of the substrate are brought into contact with each other, and hence the precursor thin-film is formed on the surface of the substrate (precursor thin-film formation step). In this case, heat may be applied by heating the substrate or heating the film formation chamber. The precursor thin-film formed in this step is a thin-film produced from the compound represented by the general formula (1) or a thin-film produced by the decomposition and/or reaction of part of the compound represented by the general formula (1), and hence has composition different from that of the target metal thin-film. The temperature of the substrate when this step is performed is preferably from room temperature to 500° C., more preferably from 100° C. to 300° C. The pressure of a system (in the film formation chamber) when this step is performed is preferably from 1 Pa to 10,000 Pa, more preferably from 10 Pa to 1,000 Pa.

Next, the unreacted compound gas and a gas generated as a by-product are evacuated from the film formation chamber (evacuation step). It is ideal that the unreacted compound gas and the gas generated as a by-product be completely evacuated from the film formation chamber, but it is not always required that the gases be completely evacuated. As an evacuation method, there are given, for example: a method including purging the inside of the system with an inert gas, such as nitrogen, helium, or argon; a method including performing evacuation by decompressing the inside of the system; and a combination of these methods. The degree of decompression when the decompression is performed is preferably from 0.01 Pa to 300 Pa, more preferably from 0.01 Pa to 100 Pa.

Next, a reducing gas is introduced as the reactive gas into the film formation chamber, and the metal thin-film is formed from the precursor thin-film obtained in the previous precursor thin-film formation step through the action of the reducing gas or the action of the reducing gas and heat (metal-containing thin-film formation step). In this step, the temperature when the heat is applied is preferably from room temperature to 500° C., more preferably from 100° C. to 300° C. The pressure of the system (in the film formation chamber) when this step is performed is preferably from 1 Pa to 10,000 Pa, more preferably from 10 Pa to 1,000 Pa. The compound represented by the general formula (1) has satisfactory reactivity with the reducing gas, and hence a high-quality metal thin-film containing less residual carbon can be obtained.

When the ALD method is adopted in the method of producing a thin-film of the present invention as described above, thin-film deposition performed by a series of operations consisting of the above-mentioned raw material introduction step, precursor thin-film formation step, evacuation step, and metal-containing thin-film formation step is defined as one cycle, and this cycle may be repeated a plurality of times until a thin-film having a required film thickness is obtained. In this case, it is preferred that, after one cycle is performed, a compound gas and a reactive gas that are unreacted, and a gas generated as a by-product be evacuated from the deposition reaction portion in the same manner as in the above-mentioned evacuation step, and then the subsequent one cycle be performed.

In addition, in the formation of the metal thin-film by the ALD method, energy, such as plasma, light, or a voltage, may be applied, and a catalyst may be used. There are no particular limitations on the timing of the application of the energy and the timing of the use of the catalyst. The energy may be applied or the catalyst may be used, for example, at the time of the introduction of the compound gas in the raw material introduction step, at the time of heating in the precursor thin-film formation step or the metal-containing thin-film formation step, at the time of the evacuation of the inside of the system in the evacuation step, or at the time of the introduction of the reducing gas in the metal-containing thin-film formation step, or between the above-mentioned respective steps.

In addition, in the method of producing a thin-film of the present invention, after the thin-film deposition, annealing treatment may be performed under an inert atmosphere, an oxidizing atmosphere, or a reducing atmosphere in order to obtain more satisfactory electrical characteristics. When step embedding is required, a reflow step may be provided. The temperature in this case is from 200° C. to 1,000° C., preferably from 250° C. to 500° C.

A well-known ALD apparatus may be used in the method of producing a thin-film of the present invention. Specific examples of the ALD apparatus include an apparatus capable of performing bubbling supply of a precursor as illustrated in FIG. 1 and FIG. 3 and an apparatus including a vaporization chamber as illustrated in FIG. 2 and FIG. 4. Another specific example thereof is an apparatus capable of subjecting the reactive gas to plasma treatment as illustrated in FIG. 3 and FIG. 4. The apparatus is not limited to such single-substrate type apparatus each including a film formation chamber (hereinafter referred to as "deposition reaction portion") as illustrated in FIG. 1 to FIG. 4, and an apparatus capable of simultaneously processing a large number of substrates through use of a batch furnace may also be used. Those apparatus may also be used as CVD apparatus.

A thin-film produced through use of the thin-film forming raw material of the present invention may be formed as desired kinds of thin-films, such as thin-films of a metal, oxide ceramics, nitride ceramics, and glass, by appropriately selecting the other precursor, the reactive gas, and the production conditions. It has been known that the thin-films exhibit electrical characteristics, optical characteristics, and the like, and the thin-films have been applied to various usages. Examples thereof include a metal thin-film, a metal oxide thin-film, a metal nitride thin-film, an alloy thin film, and a metal-containing composite oxide thin-film. Those thin-films have been widely used in the production of, for example, an electrode material for a memory element typified by a DRAM element, a resistance film, a diamagnetic film used for the recording layer of a hard disk, and a catalyst material for a polymer electrolyte fuel cell.

EXAMPLES

The present invention is described in more detail below by way of the Examples, the Comparative Examples, and the Evaluation Examples. However, the present invention is by no means limited by the Examples and the like below.

<Production of Intermediate Compound>

The production results of the following intermediate compounds 1 and 2 are described in Production Examples 1 and 2 below. In the following intermediate compounds 1 and 2, "Me" represents a methyl group, "Et" represents an ethyl group, and "tBu" represents a tert-butyl group.

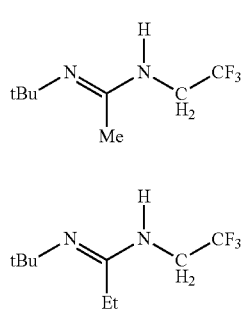

Intermediate compound 1

Intermediate compound 2

Production Example 1

Production of Intermediate Compound 1

40.2 Grams (0.25 mol) of iron chloride and 359.8 g of dichloromethane were loaded into a 500-milliliter four-necked flask, and the mixture was cooled to −25° C. in an IPA/dry ice bath. 10.4 Grams (0.25 mol) of acetonitrile was dropped into the flask, and then the mixture was stirred for 10 minutes. After that, 23.1. g (0.25 mol) of 2-methyl-2-chloropropane was dropped into the flask, and after the dropping, the temperature of the mixture was returned to room temperature, followed by its stirring for 1 hour. The mixture was cooled to −35° C. in the IPA/dry ice bath again, and 27.1 g (0.27 mol) of 2,2,2-trifluoroethylamine was dropped into the flask. The contents were caused to react with each other for 1 hour under a cooled state, and then the temperature of the resultant was returned to room temperature, followed by its stirring for 14 hours. After the stirring, an aqueous solution of sodium hydroxide was used under ice cooling to complete the reaction. An organic layer was extracted and separated, and sodium sulfate was added thereto, followed by dehydration and filtration. Desolvation was performed under slightly reduced pressure in an oil bath at 65° C. to evaporate the solvent. After that, distillation was performed in the oil bath at 75° C. under slightly reduced pressure to provide the colorless and transparent intermediate compound 1 in a yield of 42.8 g and a percent yield of 88%.

(Analysis Values)
(1) $^1$H-NMR (Solvent: Deuterated Benzene) (Chemical Shift:Multiplicity:Number of Hs)
(0.96:s:3), (1.29:s:9), (3.38-3.41:q:2)

Production Example 2

Production of Intermediate Compound 2

40.3 Grams (0.25 mol) of iron chloride and 498.7 g of dichloromethane were loaded into a 500-milliliter four-necked flask, and the mixture was cooled to −29° C. in an IPA/dry ice bath. 14.0 Grams (0.25 mol) of propionitrile was dropped into the flask, and then the mixture was stirred for 10 minutes. After that, 23.5 g (0.25 mol) of 2-methyl-2-chloropropane was dropped into the flask, and after the dropping, the temperature of the mixture was returned to room temperature, followed by its stirring for 2 hours. The mixture was cooled to −30° C. in the IPA/dry ice bath again, and 27.1 g (0.27 mol) of 2,2,2-trifluoroethylamine was dropped into the flask. The contents were caused to react with each other for 1 hour under a cooled state, and then the temperature of the resultant was returned to room temperature, followed by its stirring for 15 hours. After the stirring, an aqueous solution of sodium hydroxide was used under ice cooling to complete the reaction. An organic layer was extracted and separated, and sodium sulfate was added thereto, followed by dehydration and filtration. Desolvation was performed under slightly reduced pressure in an oil bath at 75° C. to evaporate the solvent. After that, distillation was performed in the oil bath at 85° C. under slightly reduced pressure to provide the colorless and transparent intermediate compound 2 in a yield of 41.3 g and a percent yield of 80%.

(Analysis Values)
(1) $^1$H-NMR (Solvent: Deuterated Benzene) (Chemical Shift:Multiplicity:Number of Hs)
(0.57-0.61:t:3), (1.31:s:9), (1.31-1.36:q:2), (3.45-3.50:q:2)

<Production of Amidinate Compound and Dimer Compound Thereof>

The production results of amidinate compounds and dimer compounds thereof are described in Examples 1 to 3 below.

Example 1

Production of Compound No. 19

6.0 Grams (0.046 mol) of cobalt chloride and 32.9 g of tetrahydrofuran were loaded into a 300-milliliter three-necked flask, and the mixture was stirred under room temperature. A solution prepared by using 18.5 g (0.094 mol) of the intermediate compound 1, 59.4 g of tetrahydrofuran, and 60 ml (0.094 mol) of n-BuLi was dropped into the flask under ice cooling. After the dropping, the temperature of the mixture was returned to room temperature, and the mixture was stirred for 17 hours, followed by its filtration. The solvent was removed from the resultant filtrate, and the residue was distilled at a bath temperature of 125° C., a pressure of 93 Pa, and a column top temperature of 90° C. to provide Compound No. 19 that was a dark blue solid in a yield of 12.6 g and a percent yield of 61%.

(Analysis Values)

(1) Elemental Analysis (Metal Analysis: ICP-AES)

C: 42.6 mass %, H: 6.1 mass %, Co: 13.3 mass %, F: 25.2 mass %, N: 12.8 mass %

(Theoretical values; C: 42.8 mass %, H: 6.3 mass %, Co: 13.1 mass %, F: 25.3 mass %, N: 12.5 mass %)

Example 2

Production of Compound No. 20

13.1 Grams (0.101 mol) of cobalt chloride and 70.3 g of tetrahydrofuran were loaded into a 500-milliliter three-necked flask, and the mixture was stirred under room temperature. A solution prepared by using 42.9 g (0.204 mol) of the intermediate compound 2, 63.3 g of tetrahydrofuran, and 130 ml (0.204 mol) of n-BuLi was dropped into the flask under ice cooling. After the dropping, the temperature of the mixture was returned to room temperature, and the mixture was stirred for 17 hours, followed by its filtration. The solvent was removed from the resultant filtrate, and the residue was distilled at a bath temperature of 120° C., a pressure of 110 Pa, and a column top temperature of 100° C. to provide Compound No. 20 that was a dark blue liquid in a yield of 28.6 g and a percent yield of 60%.

(Analysis Values)

(1) Elemental Analysis (Metal Analysis: ICP-AES)

C: 45.2 mass %, H: 6.6 mass %, Co: 12.6 mass %, F: 23.8 mass %, N: 11.8 mass %

(Theoretical values; C: 45.3 mass %, H: 6.7 mass %, Co: 12.4 mass %, F: 23.9 mass %, N: 11.7 mass %)

Example 3

Production of Compound No. 68

33.8 Grams (0.077 mol) of bis(trimethylsilylamide)tin and 89.2 g of normal hexane were loaded into a 300-milliliter three-necked flask, and the mixture was stirred under room temperature. 32.5 Grams (0.154 mol) of the intermediate compound 2 was dropped into the flask under ice cooling. After the dropping, the temperature of the mixture was returned to room temperature, and the mixture was stirred for 17 hours, followed by its filtration. The solvent was removed from the resultant filtrate, and the residue was purified at a bath temperature of 135° C. and a pressure of 45 Pa to provide Compound No. 68 that was a pale yellow solid in a yield of 35.4 g and a percent yield of 86%.

(Analysis Values)

(1) $^1$H-NMR (Solvent: Deuterated Benzene) (Chemical Shift:Multiplicity:Number of Hs)

(0.76-0.79:t:3), (1.17:s:9), (2.06-2.12:q:2), (3.76-3.83:q:2)

(2) Elemental Analysis (Metal Analysis: ICP-AES)

C: 40.0 mass %, H: 6.2 mass %, Sn: 22.3 mass %, F: 21.1 mass %, N: 10.4 mass %

(Theoretical values; C: 40.3 mass %, H: 6.0 mass %, Sn: 22.1 mass %, F: 21.2 mass %, N: 10.4 mass %)

Evaluation Examples

The compounds of the present invention obtained in Examples 1 to 3 and Comparative Compounds 1 and 2 below were subjected to the following evaluations. In Comparative Compounds 1 and 2 below, "Me" represents a methyl group, "Et" represents an ethyl group, and "tBu" represents a tert-butyl group.

(1) Melting Point Evaluation

The state of each of the compounds at 20° C. was visually observed. Regarding a compound that was a solid at 20° C., its melting point was measured with a minute melting point-measuring device. A compound having a low melting point is excellent in transportability, and hence can be judged to be preferred as a thin-film forming raw material. A compound that is in a liquid state at 20° C. is particularly excellent in transportability, and hence can be judged to be particularly preferred as a thin-film forming raw material. The results are shown in Table 1.

(2) Temperature (° C.) at the Time of 50 Mass % Loss in Normal Pressure TG-DTA

The weight of a test compound was measured with a TG-DTA under normal pressure at an Ar flow rate of 100 mL/min and a temperature increase rate of 10° C./min in the scanning temperature range of from 30° C. to 600° C., and the temperature (° C.) at which the weight of the test compound reduced by 50 mass % was evaluated as a "temperature (° C.) at the time of a 50 mass % loss in normal pressure TG-DTA." The results are shown in Table 1.

(3) Temperature (° C.) at the Time of 50 Mass% Loss in Reduced Pressure TG-DTA

The weight of a test compound was measured with a TG-DTA at 10 Torr, an Ar flow rate of 50 mL/min, and a temperature increase rate of 10° C./min in the scanning temperature range of from 30° C. to 600° C., and the temperature (° C.) at which the weight of the test compound reduced by 50 mass % was evaluated as a "temperature (° C.) at the time of a 50 mass % loss in reduced pressure TG-DTA." The results are shown in Table 1.

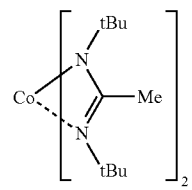

Comparative Compound 1

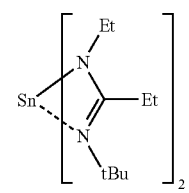

Comparative Compound 2

TABLE 1

|  | Kind of M | Compound | State at 20° C. | Melting point/° C. | Temperature at time of 50 mass % loss in normal pressure TG-DTA [° C.] | Temperature at time of 50 mass % loss in reduced pressure TG-DTA [° C.] |
| --- | --- | --- | --- | --- | --- | --- |
| Evaluation Example 1 | Cobalt | No. 19 | Solid | 57 | 185 | 115 |
| Evaluation Example 2 |  | No. 20 | Liquid | — | 195 | 120 |
| Comparative Evaluation Example 1 |  | Comparative Compound 1 | Solid | 103 | 205 | 130 |
| Evaluation Example 3 | Tin | No. 68 | Solid | 65 | 200 | 125 |
| Comparative Evaluation Example 2 |  | Comparative Compound 2 | Solid | 82 | 230 | 145 |

As shown in Table 1 above, it was found that Compounds No. 19 and No. 20 were compounds each having a temperature at the time of a 50 mass % loss in normal pressure TG-DTA and a temperature at the time of a 50 mass % loss in reduced pressure TG-DTA lower than those of Comparative Compound 1 by 10° C. or more each. In addition, it was found that Compound No. 68 was a compound having a temperature at the time of a 50 mass % loss in normal pressure TG-DTA lower than that of Comparative Compound 2 by 30° C. and having a temperature at the time of a 50 mass % loss in reduced pressure TG-DTA lower than that of Comparative Compound 2 by 20° C. In other words, it was found that the amidinate compound and the dimer compound thereof of the present invention were compounds having vapor pressures larger than those of an amidinate compound and a dimer compound thereof that had heretofore been known. In addition, it was found that Compounds No. 19 and No. 20 were compounds each having a melting point lower than that of Comparative Compound 1 by 45° C. or more. It was found that Compound No. 20 was a liquid at 20° C., and was hence a compound having a particularly low melting point. In addition, it was found that Compound No. 68 was a compound having a melting point lower than that of Comparative Compound 2 by 15° C. or more.

<Production of Thin-Films by ALD Method>

A metal cobalt thin-film or a tin oxide thin-film was produced on a silicon substrate by the ALP method under the following conditions through use of an ALD apparatus illustrated in FIG. 1 with each of the compounds of the present invention obtained in Examples 1 to 3 and Comparative Compounds 1 and 2, being used as a chemical vapor deposition raw material. Regarding each of the obtained thin-films, a film thickness was measured by an X-ray reflectivity method, a compound of the thin-film was identified by an X-ray diffraction method, and the content of carbon in the thin-film was measured by X-ray photoelectron spectroscopy. The results are shown in Table 2.

Examples 4 and 5, and Comparative Example 1

Production of Metal Cobalt Thin-films by ALD Method
(Conditions)
Reaction temperature (substrate temperature): 200° C.
Reactive gas: hydrogen
(Steps)
A series of steps consisting of the following steps (1) to (4) was defined as one cycle, and this cycle was repeated 600 times:
(1) vapor of a chemical vapor deposition raw material vaporized under the conditions of a raw material vessel heating temperature of 80° C. and a raw material vessel internal pressure of 100 Pa is introduced, and the raw material is deposited at a system pressure of 100 Pa for 30 seconds;
(2) an unreacted raw material is removed through argon purging for 45 seconds;
(3) a reactive gas is introduced and subjected to a reaction at a system pressure of 100 Pa for 10 seconds; and
(4) an unreacted raw material is removed through argon purging for 15 seconds.

Example 6 and Comparative Example 2

Production of Tin Oxide Thin-film by ALD Method
(Conditions)
Reaction temperature (substrate temperature): 150° C.
Reactive gas: water vapor
(Steps)
A series of steps consisting of the following steps (1) to (4) was defined as one cycle, and this cycle was repeated 700 times:
(1) vapor of a chemical vapor deposition raw material vaporized under the conditions of a raw material vessel heating temperature of 80° C. and a raw material vessel internal pressure of 100 Pa is introduced, and the raw material is deposited at a system pressure of 100 Pa for 20 seconds;
(2) an unreacted raw material is removed through argon purging for 15 seconds;
(3) a reactive gas is introduced and subjected to a reaction at a system pressure of 100 Pa for 0.4 second; and
(4) an unreacted raw material is removed through argon purging for 90 seconds.

TABLE 2

| | Chemical vapor deposition raw material | Thickness of thin-film | Compound of thin-film | Carbon content in thin-film |
|---|---|---|---|---|
| Example 4 | No. 19 | 7.0 nm | Metal cobalt | Undetectable[*1] |
| Example 5 | No. 20 | 7.5 nm | Metal cobalt | Undetectable[*1] |
| Comparative Example 1 | Comparative Compound 1 | 3.5 nm | Metal cobalt | 6 atm % |
| Example 6 | No. 68 | 6.5 nm | Tin oxide | Undetectable[*1] |
| Comparative Example 2 | Comparative Compound 2 | 3.0 nm | Tin oxide | 5 atm % |

[*1]The detection limit is 0.1 atm %.

The content of carbon in the metal thin-film obtained by the ALD method is 5 atm % or more in each of Comparative Examples 1 and 2, whereas the content of carbon is less than 0.1 atm % that is the detection limit in each of Examples 4 to 6. In other words, it was shown that a high-quality metal thin-film was obtained through use of each of the amidinate compound and the dimer compound thereof of the present invention. In addition, the thickness of the obtained thin-film is 3.5 nm or less in each of Comparative Examples 1 and 2, whereas the thickness is 6.5 nm or more in each of Examples 4 to 6. Thus, the metal thin-film was obtained with high productivity through use of each of the amidinate compound and the dimer compound thereof of the present invention. In particular, Compound No. 20 was a liquid at 20° C., and the metal thin-film was able to be obtained with particularly high productivity when Compound No. 20 was used as a chemical vapor deposition raw material, and hence it was shown that Compound. No. 20 was particularly excellent as a chemical vapor deposition raw material.

The invention claimed is:

1. An amidinate compound, which is represented by the following general formula (1), or a dimer compound thereof:

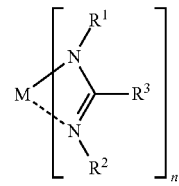

(1)

Wherein,
- $R^1$ represents a 2,2,2-trifluoroethyl group;
- $R^2$ represent an alkyl group having 1 to 5 carbon atoms;
- $R^3$ represents a hydrogen atom or an alkyl group having 1 to 5 carbon atoms;
- M represents a copper atom, a cobalt atom, a nickel atom, a manganese atom, a zinc atom, a tin atom, an yttrium atom, an indium atom, a titanium atom, a gallium atom, or a silicon atom; and
- "n" represents a valence of the atom represented by M.

2. A thin-film forming raw material, comprising the amidinate compound or the dimer compound thereof of claim 1.

3. A method of producing a thin-film containing a metal atom or a silicon atom on a surface of a substrate, the method comprising the steps of:
- vaporizing the thin-film forming raw material of claim 2;
- introducing vapor containing the amidinate compound represented by the general formula (1) or the dimer compound thereof, which has been vaporized, into a treatment atmosphere; and
- subjecting the compound to decomposition and/or a chemical reaction to form the thin-film containing the metal atom or the silicon atom on the surface of the substrate.

* * * * *